United States Patent [19]

Krotine

[11] Patent Number: 4,813,094
[45] Date of Patent: Mar. 21, 1989

[54] DISPOSABLE GENITAL CLEANER

[76] Inventor: Michael L. Krotine, 805 E. 200th St., Euclid, Ohio 44119

[21] Appl. No.: 147,802

[22] Filed: Jan. 25, 1988

[51] Int. Cl.$^4$ ............................................. A47K 7/02
[52] U.S. Cl. ............................... 15/244.1; 15/244.4; 604/1; 604/289
[58] Field of Search ............... 15/244.4, 244.1; 604/1, 604/2, 3, 289, 310, 349, 351; 401/132, 134

[56] References Cited

U.S. PATENT DOCUMENTS

| 1,270,536 | 6/1918 | Maher | 15/244.4 |
| 3,054,403 | 9/1962 | Baker | 604/2 |
| 3,577,990 | 5/1971 | Borgerson | 604/349 |
| 3,876,314 | 4/1975 | Nehring | 604/289 X |
| 4,148,318 | 4/1979 | Meyer | 604/3 |
| 4,401,130 | 8/1983 | Halford | 604/1 X |
| 4,589,875 | 5/1986 | Stringer | 604/351 |

Primary Examiner—Harvey C. Horsby
Assistant Examiner—K. O'Leary
Attorney, Agent, or Firm—Baldwin, Egan & Fetzer

[57] ABSTRACT

An inexpensive, disposable genital cleaning device comprising of a non-absorbing, splinter free, rod-like handle and a specially cut delicate, synthetic foam scrub member which can be pre-treated with an antiseptic. A safe, cleaning device designed to adapt to both the male and female genitalia. This is accomplished by the top point being convex shaped with a concave shape along the underside.

4 Claims, 1 Drawing Sheet

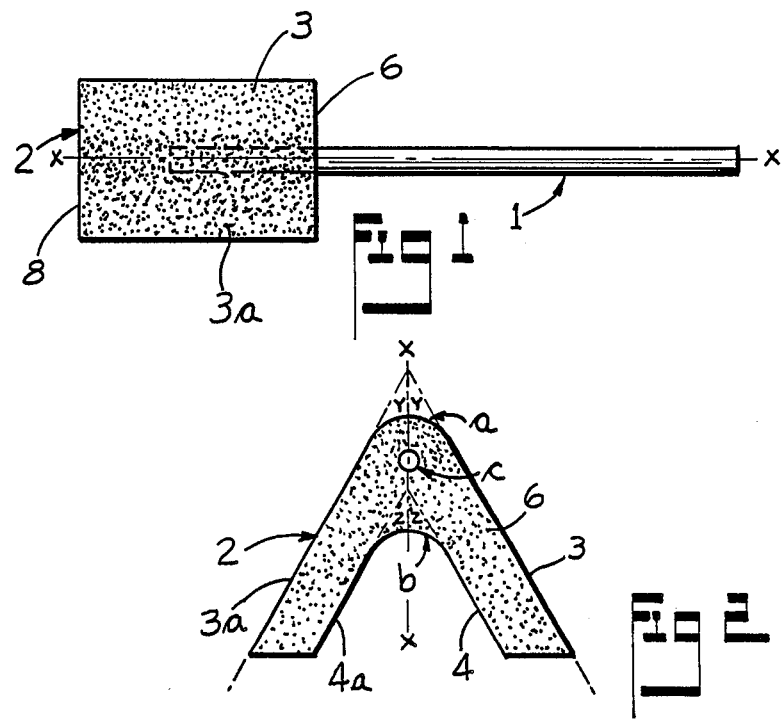
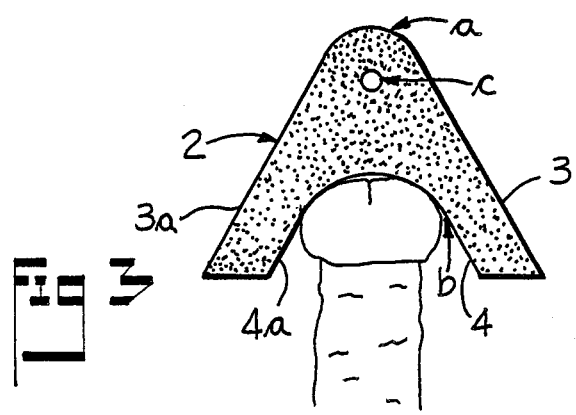
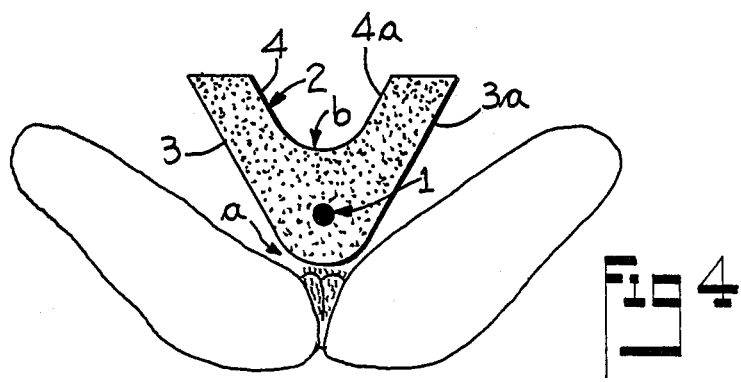

DISPOSABLE GENITAL CLEANER

The invention to be hereby described is a disposable as well as an inexpensive cleaning device, designed specifically to wash and sanitize both the male and female genitalia. A device which would be disposed of after a one time use. Also, it is a gentle cleaning device which would allow a user to exercise basic hygiene without risk of actual contact and possible spread of disease. Today, with the widespread contraction of genital oriented diseases such as Aides, Syphillis, Gonorrhea, and Herpes, there is a definite need for a simple but yet effective cleaning device. Also, it is one which would permit usage which is free from risk of contact with the individuals hand on the genital area. The goal of this invention is to provide optional application to both the male and/or female genitals in a sanitized, disposable package. The device offers the simplicity of a two piece system. First, a synthetic foam cleaning member designed to fit the penis along one side and can be iserted within the vaginal area with the opposite side. Secondly, a non-absorbing, splinter free, rod-like handle to which the foam cleaning member is adhered. The foam cleaning member may be pre-treated with a suitable antiseptic sterilizing compound. The drawings to follow will provide a more detailed and comprehendable analysis.

BRIEF DESCRIPTION OF THE DRAWINGS

FIG. 1 - A top plan view displaying a profile of the invention.

FIG. 2 - An end view of the device.

FIG. 3 - An end view of the device commencing engagement with the penis.

FIG. 4 - An enlarged end view (a) of the foam scrub member commencing engagement within the female genitalia.

DETAILED DESCRIPTION

FIG. 1 shows the device in entirety as an elongated handle (1), one which must be splinter free and non-absorbing to avoid degradation over long time packaging and shelf life. Adhered to one end of the said handle (1) is a specially designed scrub member (2) formed from a delicate, synthetic foam material. FIG. 2 shows an end elevational view of the device and illustrates the unique dual cleaning design. Portion (a) designates a convex shaped edge for cleaning the vagina. Portion (b) designates the underlying portion of the foam scrub member with a concave shape to partially surround the penis during cleaning. FIG. 3 shows specifically, portion (b) of scrub member (2) engaged along with and across the end of the penis. FIG. 4 shows specifically portion (a) of scrub member (2) engaged parallel with the length of the vaginal area. FIG. 2 illustrates said scrub member (2) consisting of one side being convex shaped (a) at such an angle so to permit comfortable but yet effective cleaning action when drawn back and forth across and along the length within the vaginal area. Also, FIG. 2 illustrates said scrub member (2) consisting of the opposite side (b) being concave within two opposing angles (e.g. Z,Z) so as to permit the same comfortable cleansing action while being applied across and along the length of the penis. An antiseptic agent may be included within the scrub member (2) by means of saturation prior to packaging. FIG. 1 illustrates the simplicity in a two piece system. The handle portion (1) should be manufactured from either a plastic rod or tube. Any safe, non-toxic adhesive can be applied to one end and allow adhesion of both handle (1) and scrub member (2).

The scrub member (2) shall be of a delicate, synthetic foam material intentionally selected for comfort when applied to such sensitive portions of the body. Opposing angles (e.g. Y,Y) along both top (a) and bottom (b) e.g. angles Z,Z may be obtained by die cutting or any similar cutting operation. The scrub member (2) shall have a hole (c) cut or drilled into and through the center, parallel to the length of said scrub member. The rod-like handle (1) shall then be inserted and adhered into this area at one time. The invention hereby stated is designed primarily for one time usage and then to be disposed of. Also, it is one which can be manufactured and assembled in an automated manner. The device can be manufactured easily as well as inexpensively. Packing would present the device in an airtight sanitary wrapper or container. Effective cleaning can be obtained by the user without risk of possible contact and spread of contagious disease.

It will be seen therefore that the invention provides a disposable genital cleaning device having a non-absorbing, splinter-free elongated handle portion (1) and a convex section (a) and concave section (b) shaped scrub member (2), and of generally rectilinear configuration when viewed in plan, and made from a delicate, synthetic, foam material or the like, intended in use to adjoin with both the male and the female genital areas during cleaning thereof, with the scrub member (2) including four generally planar sides (3, 3a, 4 and 4a), each pair of which (e.g. 3, 3a and 4, 4a) merges with the respective convex section (a) and concave section (b). The scrub member (2) also includes opposite end surfaces (6, 8) which extend generally transverse to the four sides (3, 3a, 4, 4a) and connect the latter. The scrub member (2) is secured to one end of the handle portion (1), the latter extending from a respective one of the end surfaces (6, 8). As can be best seen from FIG. 2, the scrub member (2) defines from the convex section (a) to concave section (b) opposing angles (y, y and Z, Z) along the four sides of the scrub member (2) with such angles (y, y and Z, Z) being defined by planes containing the respective of each of the four sides 3, 3a, 4, 4a) and disposed obliquely with respect to a longitudinal vertical plane (X—X) passing through the lengthwise axis of the handle portion 1.

It is my intention to make it known that I do not consider the invention previously described to be limited by myself according to any specifications listed and any future modifications may be introduced by those skilled in the art to which the invention is associated; but do claim as my invention all such improvements, adjustments and variations coming with the scope of the appended claim.

I claim:

1. A disposable genital cleaning device having a non-absorbing, splinter-free, elongated handle portion (1) and a convex section (a) and concave section (b) shaped scrub member (2) of generally rectilinear configuration when viewed in plan, and made from a delicate, synthetic, foam material and the like, intended in use to adjoin with both the male and female genital areas during cleaning thereof, wherein the convex section is shaped for cleaning the female genital area and the concave section is shaped for cleaning the male genital area; said scrub member (2) including four generally planar sides each pair of which merges with the respective said convex section and said concave section, said scrub member also including oposite end surfaces extending generally transverse to said four sides and conecting the latter, said scrub member being adhered to one end of said handle portion (1) the latter extending from a respective one of said end surfaces; also, said scrub member (2) defining from the convex section (a) to concave section (b) opposing angles along said four sides, said angles being defined by planes containing the respective of each said four sides and disposed obliquely with respect to a longitudinal vertical plane passing through the lengthwise axis of said handle portion (1).

2. A device in accordance with claim 1 wherein said handle portion extends generally perpendicularly from said one end surface.

3. A device in accordance with claim 1 wherein said four sides extend longitudinally generally parallel to the lengthwise axis of said handle portion.

4. *A device in accordance with claim 1 which is of generally V-shaped or inverted V-shaped configuration in end elevation.*

* * * * *